United States Patent [19]

Charpentier et al.

[11] Patent Number: 5,747,530
[45] Date of Patent: May 5, 1998

[54] AROMATIC DIBENZOFURAN COMPOUNDS AND PHARMACEUTICAL/COSMETIC COMPOSITIONS COMPRISED THEREOF

[75] Inventors: Bruno Charpentier, Biot; Bruno Bernard, Neuilly sur Seine, both of France

[73] Assignee: Centre International de Recherches Dermatologiques Galderma, Valbonne, France

[21] Appl. No.: 550,335

[22] Filed: Oct. 30, 1995

[30] Foreign Application Priority Data

Oct. 28, 1994 [FR] France ................... 94 12989

[51] Int. Cl.$^6$ ................ A01N 43/08; C07D 311/78; C07D 405/00
[52] U.S. Cl. .................. 514/468; 514/444; 514/337; 549/383; 549/60; 546/284.1
[58] Field of Search ................... 514/468, 444, 514/337; 549/383, 60; 546/284.1

[56] References Cited

U.S. PATENT DOCUMENTS

| | | | |
|---|---|---|---|
| 4,775,663 | 10/1988 | Forestier et al. | 514/25 |
| 5,055,452 | 10/1991 | Forestier et al. | 514/25 |
| 5,075,331 | 12/1991 | Lang et al. | 514/468 |

FOREIGN PATENT DOCUMENTS

| | | |
|---|---|---|
| 0360637 | 3/1990 | European Pat. Off. |
| 2187455 | 9/1987 | United Kingdom. |

Primary Examiner—C. Warren Ivy
Assistant Examiner—Lyman H. Smith

[57] ABSTRACT

Novel pharmaceutically/cosmetically-active dibenzofuran compounds have the structural formula (I):

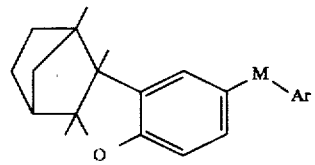

(I)

wherein Ar is a radical having one of the formulae (II) to (VI):

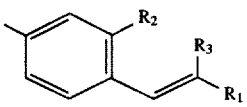

(II)

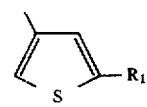

(III)

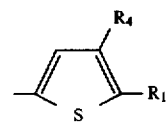

(IV)

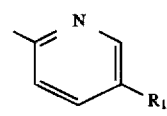

(V)

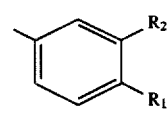

(VI)

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

44 Claims, No Drawings

AROMATIC DIBENZOFURAN COMPOUNDS AND PHARMACEUTICAL/COSMETIC COMPOSITIONS COMPRISED THEREOF

BACKGROUND OF THE INVENTION

Technical Field of the Invention

The present invention relates to novel polycyclic aromatic dibenzofuran compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and of cell proliferation, and are particularly useful in the topical and systemic treatment of dermatological conditions associated with a keratinization disorder, dermatological (or other) afflictions including an inflammatory, viral and/or immunoallergic component, and dermal or epidermal proliferations, whether benign or malignant. The subject compounds can, in addition, be used for the treatment of degenerative diseases of the connective tissue, for controlling or combating aging of the skin, whether photoinduced or chronologic, and for treating disorders of cicatrization. They are also useful for ophthalmological applications, in particular for the treatment of corneopathies.

The compounds according to the invention can also be formulated into cosmetic compositions, especially for body and hair care/hygiene.

Briefly, the aromatic dibenzofuran compounds according to this invention have the following structural formula (I):

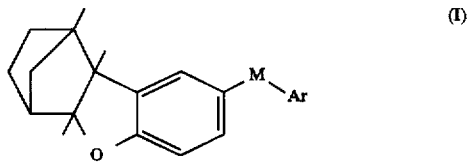

(I)

in which Ar is a radical selected from among those of the following formulae (II)–(VI):

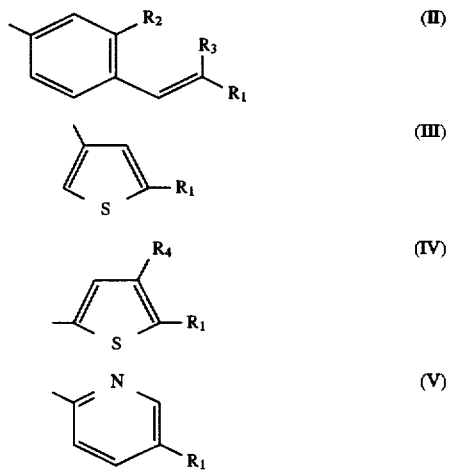

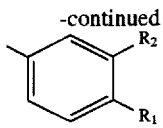

(VI)

wherein M is a bivalent radical selected from among those of the following formulae (with the proviso that said formulae can be oriented from left to right or vice versa):

 (a)

 (b)

 (c)

 (d)

 (e)

with the further proviso that, when M is a radical of formula (a), Ar cannot be a radical of formula (VI); $R_1$ is:
(i) a hydrogen atom,
(ii) the —$CH_3$ radical,
(iii) a radical —$(CH_2)_m$—O—$R_8$,
(iv) a radical —$OR_8$,
(v) a radical

(vi) a radical —$S(O)_t R_9$, with m, t, $R_8$ and $R_9$ having the definitions given below; $R_2$ is a hydrogen atom or a radical —$OR_8$, with $R_8$ having the definition given below; $R_3$ is a hydrogen atom or a lower alkyl radical; $R_4$ has the same definition as $R_1$, with the proviso that at least one of the two radicals $R_1$ and $R_4$ is a hydrogen atom; $R_5$ and $R_6$ are independently a hydrogen atom, a lower alkyl radical or a radical —$(X)_n$—$(CH_2)_p$—$R_7$, with the proviso that $R_5$ and $R_6$ may together form an oxo (=O) group, a thioxo (=S) or oxime group, a group ($R_{11}$—O—N=), an epoxy or cyclopropyl group, a cycloalkyl group optionally substituted by a halogen atom or a lower alkyl radical, or a dioxolane (—O—$(CH_2)_q$O—) group wherein q is equal to 2 or 3, with X, n, p, $R_7$ and $R_{11}$ having the definitions given below; $R_7$ is a hydrogen atom or a radical —$(CO)_r$—$R_{10}$, with r and $R_{10}$ having the definitions given below; $R_8$ is a hydrogen atom, a lower alkyl radical or a lower acyl radical; $R_9$ is (i) a hydrogen atom, (ii) a radical —N(R'R"), or (iii) a radical —$OR_{11}$, with R', R" and $R_{11}$ having the definitions given below; $R_{10}$ is a hydrogen atom, an alkyl radical, an alkenyl radical, an alkynyl radical, an aryl radical, a radical —$OR_{11}$, or a radical —N(R'R"), with R', R" and $R_{11}$ having the definitions given below; $R_{11}$ is a hydrogen atom, an alkyl radical having from 1 to 20 carbon atoms, a mono- or polyhydroxyalkyl radical, an optionally substituted aryl or optionally substituted aralkyl radical, a sugar residue or an amino acid or peptide residue; R' and R", which may be identical or different, are each a hydrogen atom, a lower alkyl radical, a mono- or polyhydroxyalkyl radical, an optionally substituted aryl radical, an optionally substituted aralkyl radical or an amino acid or peptide or sugar residue, with the proviso that R' and R" may together form a heterocycle; W is an oxygen or sulfur atom or a group —$NR_{12}$, with $R_{12}$ having the definition given below; $R_{12}$ is a hydrogen atom or a —$CH_3$ radical; X and Y are independently an oxygen atom or a sulfur atom; m and p, which are integers, vary independently from 0 to 10, with the proviso that when $R_7$ is a radical —(CO)$_r$—$R_{10}$ and $R_{10}$ is a radical —$OR_{11}$, p cannot be 0; n and r independently have the value 0 or 1; and t is equal to 0, 1 or 2.

This invention also features the optical and geometrical isomers of the compounds of formula (I), as well as their salts in the event that $R_1$, $R_4$ or $R_7$ represents an acid function.

When the compounds according to the invention are in the form of salts, by addition of a base, the salts are preferably those of an alkali metal or alkaline earth metal, or, alternatively, zinc salts or salts of an organic amine.

When the compounds of the invention are in the form of salts by addition of an acid, the salts are pharmaceutically or cosmetically acceptable salts of an inorganic or organic acid, in particular of hydrochloric, sulfuric, acetic, citric, fumaric, hemisuccinic, maleic and mandelic acids.

DETAILED DESCRIPTION OF BEST MODE AND PREFERRED EMBODIMENTS OF THE INVENTION

More particularly according to the present invention, by "lower alkyl radical" is intended an alkyl radical having from 1 to 6 carbon atoms, and preferably methyl, ethyl, isopropyl, butyl, tert-butyl and hexyl radicals.

By "alkenyl radical" is intended a linear or branched radical having from 2 to 20 carbon atoms and containing at least one ethylenic double bond.

By "alkynyl radical" is intended a linear or branched radical having from 2 to 20 carbon atoms and containing at least one acetylenic triple bond.

By "lower acyl radical" is intended a radical having from 1 to 6 carbon atoms, and preferably acetyl, propionyl and pivaloyl radicals.

By "alkyl radical" is intended a linear or branched radical having from 1 to 20 carbon atoms, optionally substituted by one or more fluorine atoms.

By "monohydroxyalkyl radical" is intended a radical having from 1 to 6 carbon atoms, in particular a 2-hydroxyethyl, 2-hydroxypropyl or 3-hydroxypropyl radical.

By "polyhydroxyalkyl radical" is intended a radical having from 2 to 6 carbon atoms and from 2 to 5 hydroxyl groups, such as 2,3-dihydroxypropyl, 2,3,4-trihydroxybutyl and 2,3,4,5-tetrahydroxypentyl radicals, or the pentaerythritol residue.

By "aryl radical" is preferably intended a phenyl radical optionally substituted by one or more halogen atoms, a hydroxyl or nitro functional group, or a methoxy group.

By "aralkyl radical" is intended a benzyl or phenethyl radical, optionally substituted by one or more halogen atoms, a hydroxyl or nitro functional group, or a methoxy group.

By "amino acid residue" is intended a residue derived, for example, from one of the 20 amino acids of L or D configuration from which mammalian proteins are constructed.

By "peptide residue" is intended a linear peptide comprising from 2 to 10 amino acids.

By "sugar residue" is intended a residue derived, for example, from glucose, from galactose, from mannose or from glucuronic acid.

Lastly, by "heterocycle" is preferably intended a piperidino, morpholino, pyrrolidino or piperazino radical, optionally substituted at the 4-position by a $C_1$–$C_6$ alkyl radical, or a mono- or polyhydroxyalkyl radical as defined above.

Among the compounds of formula (I), preferred are those compounds corresponding to the formula (I) in which M is a radical of formula (e) wherein W is an oxygen atom and Ar is a radical of formula (VI); they may thus be represented by the formula (Ia):

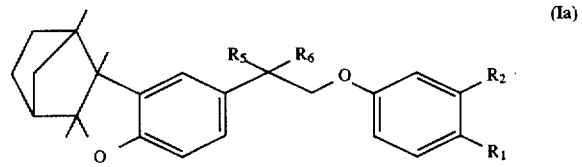

in which $R_1$, $R_2$, $R_5$ and $R_6$ are as defined above.

Among the compounds of general formula (I), particularly representative are the following:

Methyl 4-[(E)-3-(1,2,3,4-tetrahydro-1,4a,9b-trimethyl-1,4-methanodibenzofuran-8-yl)-3-oxo-1-propenyl]benzoate;

4-[(E)-3-(1,2,3,4-Tetrahydro-1,4a,9b-trimethyl-1,4-methanodibenzofuran-8-yl)-3-oxo-1-propenyl]benzoic acid;

Methyl 4-[(E)-3-(1,2,3,4-tetrahydro-1,4a,9b-trimethyl-1,4-methanodibenzofuran-8-yl)-3-oxo-1-propynyl]benzoate;

4-[(E)-3-(1,2,3,4-Tetrahydro-1,4a,9b-trimethyl-1,4-methanodibenzofuran-8-yl)-3-oxo-1-propynyl]benzoic acid;

Benzyl 4-[2-(1,2,3,4-tetrahydro-1,4a,9b-trimethyl-1,4-methanodibenzofuran-8-yl)-2-oxoethoxy]benzoate;

4-[2-(1,2,3,4-Tetrahydro-1,4a,9b-trimethyl1,4-methanodibenzofuran-8-yl)-2-oxoethoxy]b acid;

4-[2-(1,2,3,4-Tetrahydro-1,4a,9b-trimethyl1,4-methanodibenzofuran-8-yl)-2-hydroxyethoxy]benzoic acid;

Benzyl 4-[2-(1,2,3,4-tetrahydro-1,4a,9b-trimethyl-1,4-methanodibenzofuran-8-yl)-2-oxoethoxy]-2-hydroxybenzoate;

4-[[2-(1,2,3,4-Tetrahydro-1,4a,9b-trimethyl1,4-methanodibenzofuran-8-yl)-2-oxoethoxy]-2-hydroxybenzoic acid;

4-[[2-(1,2,3,4-Tetrahydro-1,4a,9b-trimethyl1,4-methanodibenzofuran-8-yl)-2-hydroxyethoxy]-2-hydroxybenzoic acid;

4-[2-(1,2,3,4-Tetrahydro-1,4a,9b-trimethyl1,4-methanodibenzofuran-8-yl)ethoxy]-2-hydroxybenzoic acid;

Ethyl 4-[(1,2,3,4-tetrahydro-1,4a,9b-trimethyl-1,4-methanodibenzofuran-8-yl)carbonyl]cinnamate;

4-[(1,2,3,4-Tetrahydro-1,4a,9b-trimethyl-1,4-methanodibenzofuran-8-yl)carbonyl]cinnamic acid;

Ethyl 2-[(E)-3-(1,2,3,4-tetrahydro-1,4a,9b-trimethyl-1,4-methanodibenzofuran-8-yl)-3-oxo-1-propenyl]-4-thiophenecarboxylate;

2-[(E)-3-(1,2,3,4-Tetrahydro-1,4a,9b-trimethyl-1,4-methanodibenzofuran-8-yl)-3-oxo-1-propenyl]-4-thiophenecarboxylic acid;

4-[(E)-3-(1,2,3,4-Tetrahydro-1,4a,9b-trimethyl-1,4-methanodibenzofuran-8-yl)-3-oxo-1-propenyl]benzoic acid.

The present invention also features processes for preparing the compounds of formula (I).

In a first stage, the nucleus 1,2,3,4tetrahydro-1,4a,9b-trimethyl-1,4-methanodibenzofuran (THTMDBF) is synthesized.

This nucleus is obtained in two steps, namely, by adding o-anisyllithium to fenchone, followed by the action of phosphorus pentachloride, phosphorus tribromide or a Lewis acid. The fenchone may be dextrorotatory or laevorotatory:

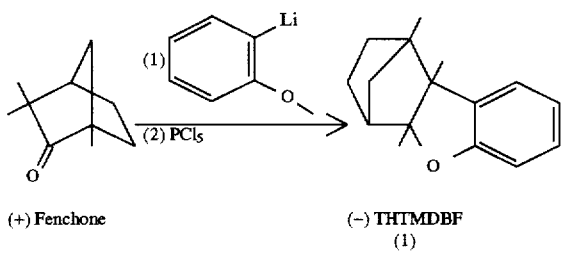

(+) Fenchone          (−) THTMDBF
(1)

This 1,2,3,4-tetrahydro-1,4a,9b-trimethyl-1,4-methanodibenzofuran nucleus is employed in the specific examples to follow without discrimination, in either its dextrorotatory or levorotatory form.

(1) The compounds of formula (I) in which M has the definition (a) may be prepared as illustrated below, either via Friedel-Crafts reaction according to the mechanism:

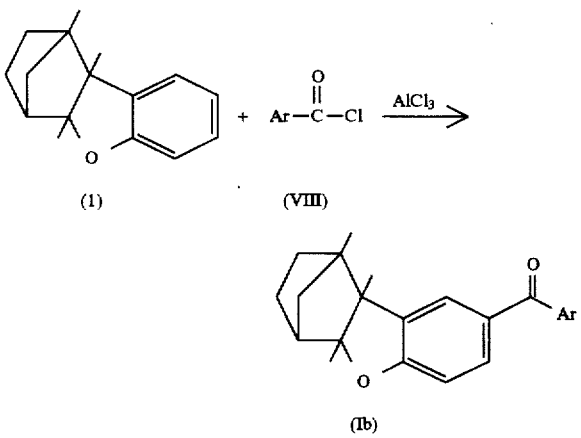

in which Ar is one of the above formulae (II) to (V); or via reaction of an organometallic derivative of THTMDBF, such as an organozinc compound or an organostannane, with a compound of formula (VIII) according to the mechanism:

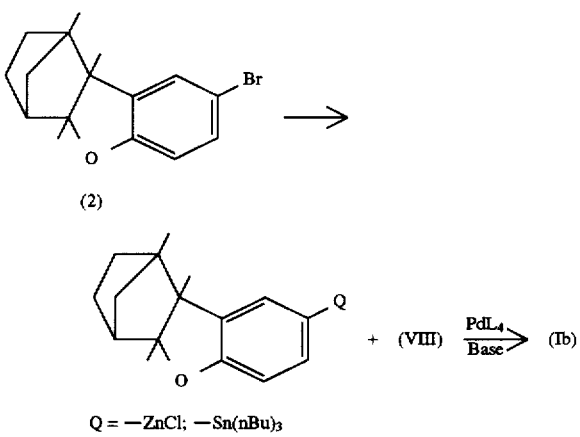

Q = —ZnCl; —Sn(nBu)$_3$ or under carbonylation conditions according to the mechanism:

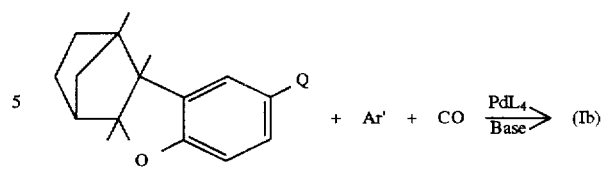

in which Ar' is as defined below:

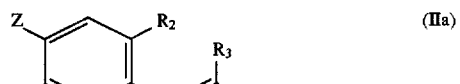

(IIa)

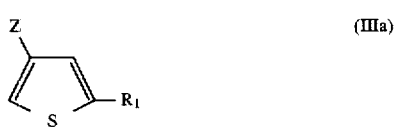

(IIIa)

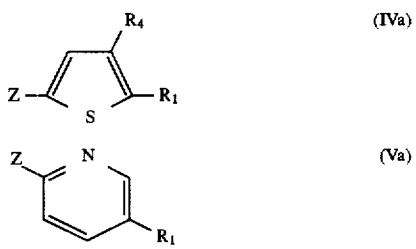

(IVa)

(Va)

In the formulae (IIa), (IIIa), (IVa) and (Va), $R_1$, $R_2$, $R_3$ and $R_4$ have the same definitions as set forth in respect of the compounds of general formula (I), and Z is Br, I or O—SO$_2$—CF$_3$.

During these reactions for the preparation of the compounds of general formula (Ib), the function $R_1$ will optionally be protected in order to be compatible with the operating conditions. The protective groups employed are those described in the text *Protecting Groups in Organic Synthesis*, by T. W. Greene, published by John Wiley and Sons (1981).

The derivative (Ib) is subsequently used as a starting material for the preparation of other compounds. These derivatives are prepared via conventional techniques of organic chemistry, such as those described in *Advanced Organic Chemistry* by J. March, John Wiley and Sons (1985).

For example, the functional modifications of the radicals $R_1$ or $R_4$ may be carried out as indicated below:
carboxylic acid→ester
ester→carboxylic acid
acid→acid chloride
acid chloride→amide
acid→amide
acid→alcohol
alcohol→aldehyde
amide→amine
thiol→thioether
thioether→sulfoxide
thioether→sulfone
sulfonic acid→sulfonic ester
sulfonic acid→sulfonamide
sulfinic acid→sulfinic ester The compounds of formula (I) in which M has the definition (a) and Ar has the formula (II), may be prepared by the following sequence: reduction of the keto acid (IX) in the presence of lithium aluminum hydride provides the diol (X), which is then oxidized to the keto carbaldehyde (XI)

with pyridinium chlorochromate. The carbaldehyde is subjected to a Horner-Hemmons reaction to provide the compounds of formula (Ic).

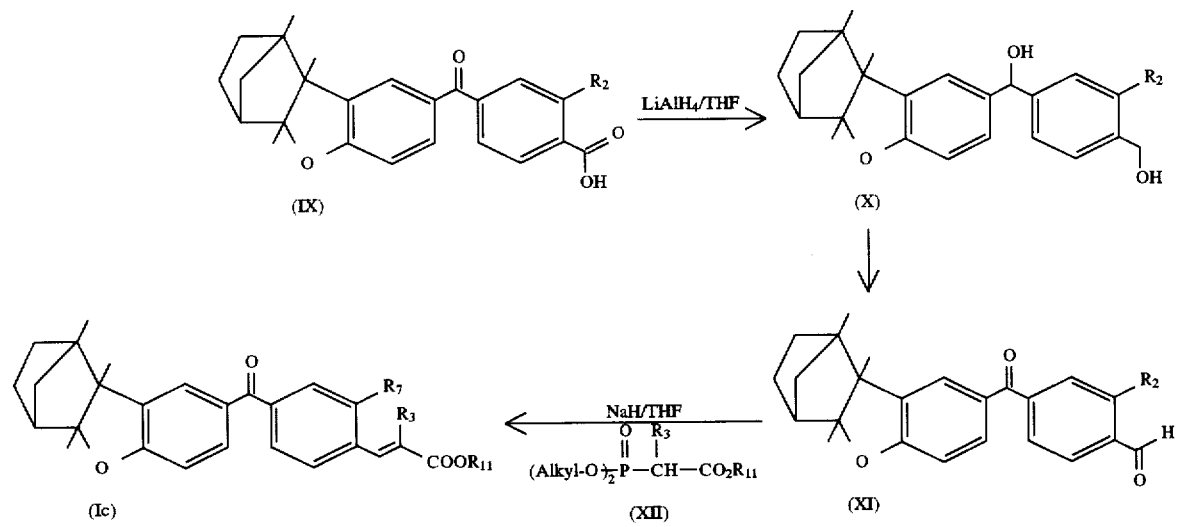

(2) The compounds of formula (I) in which M has the definition (b) may be prepared via an aldolization according to the mechanism:

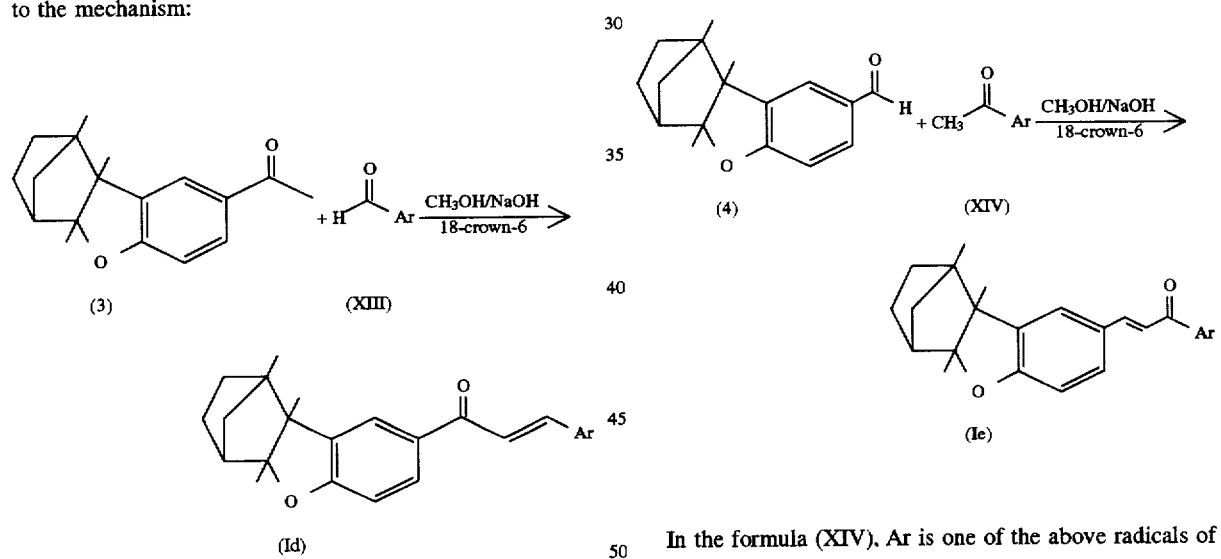

In the formula (XIII), Ar is one of the above radicals of formulae (II) to (VI), or, if (b) is in the opposite direction:

In the formula (XIV), Ar is one of the above radicals of formulae (II) to (VI).

(3) The compounds of general formula (I) in which M has the definition (c) may be prepared by condensing the trimethylsilylarylacetylene derivative with the acid chloride obtained from the derivative (5):

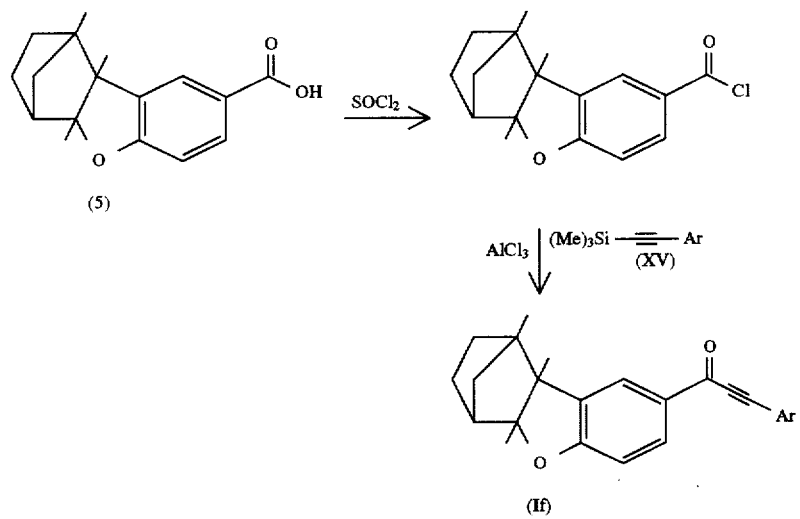

In the formula (XV), Ar is one of the above radicals of formulae (II) to (VI).

In the event that (c) is in the reverse direction, the synthesis will be carried out as illustrated below by the action of THTMDBF-acetylene under transition metal-catalyzed carbonylation conditions:

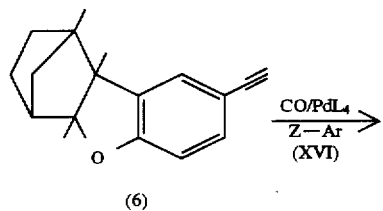

-continued

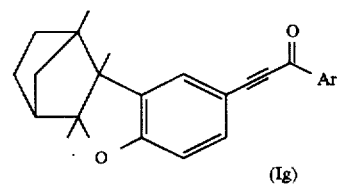

In the formula (XVI), Z has the same definition as above and Ar is one of the above radicals of formulae (II) to (VI).

(4) The compounds of general formula (I) in which M has the definition (d) may be prepared according to the following reaction mechanism:

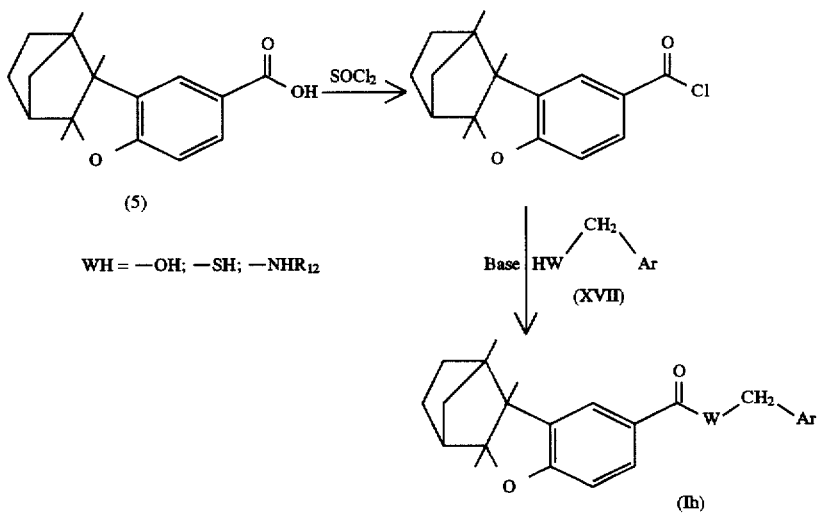

WH = —OH; —SH; —NHR$_{12}$ or, when (d) is in the reverse direction, according to the mechanism:

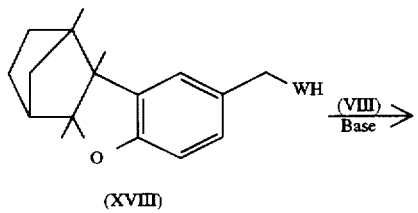

(XVIII)

WH = —OH; —SH; —NHR$_{12}$

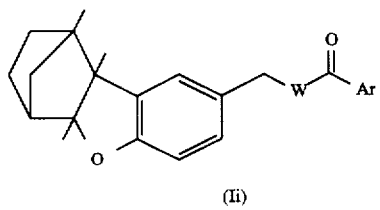

(Ii)

In the formula (VIII), Ar is one of the above radicals of formulae (II) to (VI).

In the event of the syntheses of the compounds of formula (I) in which M has the definition (d), the substituents R$_1$, R$_2$ and R$_4$ optionally present in the radical Ar are preferably suitably protected to be compatible with the coupling conditions.

This step entails reacting in an anhydrous medium, in an organic solvent such as tetrahydrofuran or methylene chloride containing a tertiary base (pyridine or triethylamine) or an alkali metal hydride (sodium hydride), an activated form of THTMDBF-carboxylic acid, such as an acid chloride or a mixed anhydride, with an aromatic compound bearing a hydroxymethyl, mercaptomethyl or tert-butoxycarbonylaminomethyl function.

In the event that M has the definition (d) with Y=S and W=NR$_{12}$, the synthesis of this thioamide derivative will be carried out using Lawesson's reagent [2,4-bis (4-methoxyphenyl)-1,3-dithia-2,4-diphosphetane 2,4-disulfide].

(5) The compounds of general formula (I) in which M has the definition (e) may be prepared according to the following reaction mechanism:

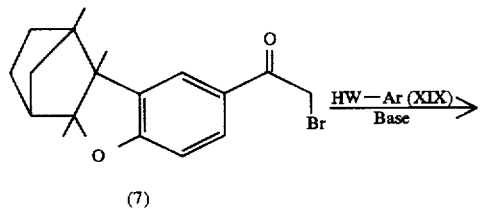

(7)

WH = —OH; —SH; —NHR$_{12}$

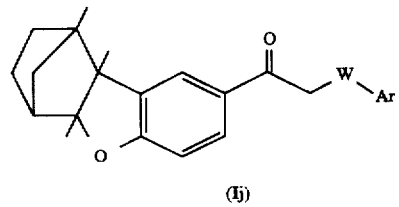

(Ij)

In the formula (XIX), Ar is one of the above radicals of formulae (II) to (VI), or, when (d) is in the reverse direction, according to the mechanism:

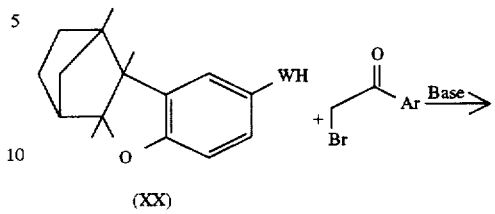

(XX)

WH = —OH; —SH; —NHR$_{12}$

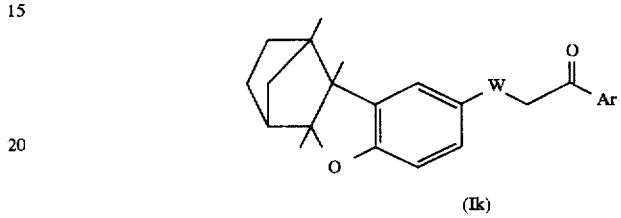

(Ik)

In the formula (XXI), Ar is one of the above radicals of formulae (II) to (VI).

The principal step in this preparative technique comprises reacting in an anhydrous medium, in an organic solvent such as DMF, an α-halo ketone with an aromatic derivative bearing an amine, phenol or thiol function, in the presence of a tertiary amine (pyridine or triethylamine) or an alkali metal hydride.

The groups R$_1$, R$_2$ and R$_4$ optionally present on the aromatic nucleus Ar are preferably protected to be compatible with these coupling conditions.

The derivatives of formulae (Ij) and (Ik) serve as starting compounds for the preparation of other compounds.

The present invention also features therapeutic/pharmaceutical applications of the compounds of formula (I).

These compounds exhibit partial antagonist or agonist activity with respect to the expression of one or more biological markers in the test of differentiation of mouse embryonic teratocarcinoma (F9) cells (Skin Pharmacol., 3, pp. 256–267 (1990)) and/or with respect to the differentiation of human keratinocytes in vitro (Skin Pharmacol., 3, pp. 70–85 (1990)) in response to retinoid treatment. These tests demonstrate the activities of the subject compounds in the fields of differentiation and proliferation. Their activities may also be measured in tests of cellular transactivation using previously transfected recombinant RAR or RXR receptors (B. A. Bernard et al, Biochemical and Biophysical Research Communications, vol. 186, pp. 977–983 (1992)); M. F. Boehm et al, Journal of Medicinal Chemistry, p37, pp. 408–414 (1994)).

The compounds according to the invention are particularly well-suited in the following fields of therapy:

(1) for treating dermatological conditions associated with a disorder of keratinization involving differentiation and proliferation, in particular for treating acne vulgaris, comedonic or polymorphic acne, rosacea, nodulocystic acne, acne conglobata, senile acne and secondary acnes such as solar, drug or occupational acne;

(2) for treating other types of disorders of keratinization, in particular ichthyoses, ichthyosiform conditions, Darier's disease, palmoplantar keratoderma, leucoplakia and leucoplakiform conditions, and cutaneous or mucosal (buccal) lichen;

(3) for treating other dermatological conditions associated with a disorder of keratinization and manifesting an inflammatory and/or immunoallergic component, and, in particular, all forms of psoriasis, whether cutaneous, mucosal or ungual, and even arthropathia psoriatica, or, alternatively, cutaneous atopy such as eczema or respiratory atopy, or, alternatively, gingival hypertrophy; the compounds may also be used for certain inflammatory conditions not involving a disorder of keratinization;

(4) for treating all dermal or epidermal proliferations, whether benign or malignant, whether or not of viral origin, such as common warts, flat warts and epidermodysplasia verruciformis, oral or florid papillomatoses and proliferations which may be induced by ultraviolet light, in particular in the case of basal cell and prickle cell epithelioma;

(5) for treating other dermatological disorders such as vesicular or bullous dermatoses and collagen diseases;

(6) for treating certain ophthalmological disorders, in particular corneopathies;

(7) for repairing and controlling/combating skin aging, whether photoinduced or chronologic, or for reducing actinic keratosis and pigmentations, or any pathology associated with chronologic or actinic aging;

(8) for preventing or treating the stigmata of epidermal and/or dermal atrophy induced by local or systemic corticosteroids, or any other form of cutaneous atrophy;

(9) for preventing or treating disorders of cicatrization, or for preventing or repairing stretch marks;

(10) for combating disorders of sebaceous function, such as hyperseborrhoea associated with acne or simple seborrhoea;

(11) for the treatment or prevention of cancerous or precancerous conditions;

(12) for the treatment of inflammatory conditions such as arthritis;

(13) for the treatment of any malady of viral origin, at the skin or general level;

(14) for the prevention or treatment of alopecia;

(15) for the treatment of dermatological or general conditions manifesting an immunological component;

(16) for the treatment of ailments or conditions of the cardiovascular system, such as arteriosclerosis;

(17) for the treatment of respiratory conditions.

For the aforesaid therapeutic or pharmaceutical applications, the compounds according to the invention may advantageously be employed in combination with other retinoids, with D vitamins or derivatives thereof or with corticosteroids, with free-radical scavengers, with α-hydroxy or α-keto acids or derivatives thereof, or, alternatively, with ion-channel blockers.

Exemplary D vitamins or derivatives thereof include the derivatives of vitamin $D_2$ or $D_3$, and especially 1,25-dihydroxy vitamin $D_3$.

Exemplary free-radical scavengers include α-tocopherol, superoxide dismutase, ubiquinol or certain metal chelating agents.

Exemplary α-hydroxy or α-keto acids or derivatives thereof include lactic, malic, citric, glycolic, mandelic, tartaric, glyceric or ascorbic acid or salicylic acid derivatives or salts, amides or esters thereof.

Exemplary ion-channel blockers include minoxidil (2,4-diamino-6-piperidinopyrimidine 3-oxide) and derivatives thereof.

The present invention thus features pharmaceutical/therapeutic compositions containing at least one compound of formula (I), or one of its optical or geometrical isomers or one of its salts or other derivatives thereof.

The pharmaceutical/therapeutic compositions of the present invention, intended especially for treating the aforesaid disease states, comprise a carrier, vehicle or diluent that is pharmaceutically acceptable, and at least one compound of formula (I), one of its optical or geometrical isomers or one of its salts or other derivatives thereof.

The administration of the compounds according to the invention may be carried out via the enteral, systemic, parenteral, topical or ocular route.

For enteral administration, the medicinal/pharmaceutical compositions may be in the form of tablets, hard gelatin capsules, dragees, syrups, suspensions, solutions, powders, granules, emulsions, polymeric or lipid microspheres or nanospheres or vesicles which permit a controlled or precision release. For parenteral administration, the compositions may be in the form of solutions or suspensions for perfusion or for injection.

The compounds according to the invention are generally administered at a daily dosage of approximately 0.01 mg/kg to 100 mg/kg body weight, and this at the regime or rate of 1 to 3 doses per diem.

For topical administration, the pharmaceutical compositions based on compounds according to the invention are more particularly intended for treatment of the skin and the mucosae, and are provided in the form of ointments, creams, milks, salves, powders, impregnated pads, solutions, gels, sprays, lotions or suspensions. They can also be provided in the form of polymeric or lipid microspheres or nanospheres or vesicles, or in the form of polymer patches or of hydrogels permitting a controlled release. These compositions for topical administration can be provided either in anhydrous form or in aqueous form, depending on the particular clinical indication.

For ocular administration, they are principally eye washes.

These compositions for topical or ocular administration contain at least one compound of formula (I), or one of its optical or geometrical isomers or one of its salts or other derivatives thereof, at a concentration preferably ranging from 0.001% to 5% by weight relative to the total weight of the composition.

The compounds of formula (I) also find application in the cosmetics field, especially in body and hair hygiene, and in particular for the treatment of skin having a tendency to develop acne, for hair regrowth and combating hair loss, for counteracting a greasy appearance of the skin or hair, in protecting the skin and hair against the adverse effects of sunlight, or in the treatment of physiologically dry skin, and for preventing and/or controlling photoinduced or chronic skin aging.

For cosmetics applications, the compounds according to the invention may advantageously be employed in combination with other retinoids, with D vitamins or derivatives thereof, with corticosteroids, with compounds that are free-radical scavengers, with α-hydroxy or α-keto acids or derivatives thereof, or, alternatively, with ion-channel blockers.

The various active agents that are advantageously formulated with the compounds of the present invention are as described above.

The present invention, therefore, also features cosmetic compositions comprising, in a cosmetically acceptable vehicle, carrier or diluent, at least one compound of formula (I), or one of its optical or geometrical isomers or one of its salts, or other derivative thereof. Such compositions are advantageously presented in the form of a cream, a milk, a lotion, a gel, polymeric or lipid microspheres or nanospheres or vesicles, a soap or a shampoo.

The concentration of the compound of formula (I) in the cosmetic compositions advantageously ranges from 0.001% to 3% by weight.

The medicinal and cosmetic compositions according to the invention may, in addition, contain inert or even pharmacodynamically or cosmetically active additives or combinations of these additives, and in particular: wetting agents; depigmenting agents such as hydroquinone, azelaic acid, caffeic acid or kojic acid; emollients; hydrating or moisturizing agents such as glycerol, PEG 400, thiamorpholinone and its derivatives or urea; anti-seborrhoeic or anti-acne agents such as S-carboxymethylcysteine, S-benzylcysteamine, their salts and other derivatives thereof, or benzoyl peroxide; antibiotics such as erythromycin and esters thereof, neomycin, clindamycin and esters thereof, or tetracyclines; antifungal agents such as ketoconazole or 4,5-polymethylene-3-isothiazolinones; agents promoting hair regrowth, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids, and in particular β-carotene; anti-psoriatic agents such as anthraline and derivatives thereof; and, lastly, eicosa-5,8,11,14-tetraynoic and eicosa-5,8,11-triynoic acids, and the esters and amides thereof.

The compositions according to the invention may also contain taste and flavor enhancers, preservatives such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

(A) SYNTHESIS OF COMPOUNDS:

Examples 1 to 7 relate to the synthesis of intermediate compounds.

Examples 8 to 23 relate to the synthesis of compounds of general formula (I).

All of the compounds whose syntheses are described below were characterized by proton NMR (250 MHz) and mass spectrometry.

EXAMPLE 1:

Preparation of 1,2,3,4-tetrahydro-1,4a,9b-trimethyl-1,4-methanodibenzofuran (THTMDBF):

50 g (0.267 mmol) of bromoanisole dissolved in 120 ml of ethyl ether were treated at 0° C. with 200 ml of n-butyllithium (1.6M in hexane), and the reaction medium was maintained under stirring at room temperature overnight. 41.57 g (273 mmol) of (+)-fenchone (Fluka) in 100 ml of ethyl ether were then added dropwise and the mixture was maintained under stirring for 6 h at room temperature. The reaction medium was poured into 200 ml of saturated ammonium chloride solution.

After extraction with 600 ml of ethyl ether, rinsing with water, drying over magnesium sulfate, filtration and evaporation, the residue was chromatographed on silica to yield 61.26 g (88%) of 2—O-anisyl-2-endo-fenchyl alcohol, melting at 62°–64° C.; $\alpha_D$=+780° (c=1, ethanol).

57.5 g (0.276 mmol) of phosphorus pentachloride were added at –10° C. to a solution of 55.24 g (0.21 mmol) of 2—O-anisyl-2-endo-fenchyl alcohol and 4 g of calcium carbonate in 800 ml of chloroform.

The reaction mixture was stirred at room temperature for two hours, potassium carbonate (30 g) was then added and the mixture was filtered. The solid residue was rinsed with chloroform and then chromatographed on silica in a hexane/$CH_2Cl_2$ (9:1) mixture to yield 31.5 g (65%) of the expected compound, melting at 68° C.; $\alpha_D$=39.5° (c=1, ethanol).

The same synthesis carried out using (–)-fenchone as the starting material yielded the dextrorotatory isomer of THTMDBF, melting at 68° C.; $\alpha_D$=+36.30 (c=1, ethanol).

EXAMPLE 2:

Preparation of 8-bromo-1,2,3,4-tetrahydro-1,4a,9b-trimethyl-1,4-methanodibenzofuran:

11.42 g (50 mmol) of (–)-1,2,3,4-tetrahydro1,4a,9b-trimethyl-1,4-methanodibenzofuran obtained in Example 1 were dissolved in 110 ml of tetrahydrofuran and were treated dropwise with a solution containing 8.9 g of N-bromosuccinimide (NBS) in 50 ml of dimethylformamide (DMF). The reaction medium was maintained under stirring at room temperature for 2 h, 30 min, then poured into ice-cold water and extracted with 500 ml of ethyl ether. After rinsing with water, drying over magnesium sulfate, filtration and evaporation, 13.8 g (90w) of the expected compound, melting at 119.8° C., were isolated after chromatography on silica in hexane; $\alpha_D$=+4.60 (c=1, chloroform).

EXAMPLE 3:

Preparation of 1,2,3,4-tetrahydro-1,4a,9b-trimethyl-1,4methanodibenzofuran-8-yl methyl ketone:

A solution containing 22.8 g (0.1 mmol) of (-)-THTMDBF and 7.8 ml (0.11 mmol) of acetyl chloride in 200 ml of dichloromethane was added dropwise to a solution of 14.67 g of aluminium chloride (0.11 mmol) in 150 ml of $CH_2Cl_2$. The reaction medium was maintained stirring for 4 h, and was then poured into ice-cold water and extracted with $CH_2Cl_2$. After conventional treatment of the organic phase followed by chromatography on silica in a hexane/ethyl ether (85:15) mixture, 17.26 g (64%) of the expected compound, melting at 140°–142° C., were isolated; $\alpha_D$=–4.3° (c=1, ethanol).

EXAMPLE 4:

Preparation of 1,2,3,4-Tetrahydro-1,4a,9b-trimethyl-1,4methanodibenzofuran-8-carbaldehyde:

13.76 g (44.8 mmol) of 8-bromo-THTMDBF obtained in Example 2 were added dropwise into a three-necked flask under nitrogen containing 1.31 g of magnesium and an iodine crystal in 5 ml of tetrahydrofuran, and the mixture was maintained under reflux for 2 h, 30 min. After the magnesium was filtered off, the reaction medium was poured into ice-cold water, acidified to pH 1 with concentrated hydrochloric acid and extracted with ether. The organic phase was washed with water, dried over magnesium sulfate, filtered and evaporated to yield 8.47 g (74%) of the expected compound, melting at 144.7° C.; $\alpha_D$=–7° (c=1, chloroform).

EXAMPLE 5:

Preparation of 1,2,3,4-tetrahydro-1,4a,9b-trimethyl-1,4methanodibenzofuran-8-carboxylic acid:

622 mg of magnesium and an iodine crystal were placed in a 250 ml three-necked flask under nitrogen, a solution containing 6.55 g (21 mmol) of 8-bromo-THTMDBF obtained in Example 2 in 70 ml of tetrahydrofuran was added dropwise while heating and the mixture was maintained under reflux for 2 hours.

The reaction medium was then cooled to −70° C., saturated with carbon dioxide and permitted to return to room temperature overnight.

After treatment, the reaction medium was poured into ice-cold water, acidified to pH 1 with concentrated hydrochloric acid and extracted with ether. After treatment of the organic phase, the residue was recrystallized in hexane to yield 4.30 g (75w) of the expected compound, melting at 290°–292° C.; $\alpha_D$=−24.4° (c=1, dimethylformamide).

EXAMPLE 6:

Preparation of 8-ethynl-1,2,3,4-tetrahydro-1,4a,9b-trimethyl-1,4-methanodibenzofuran:

30.5 ml of n-butyllithium (1.6M in hexane) were added dropwise at −780° C. under argon to a solution of 6.90 ml of diisopropylamine in 70 ml of dry tetrahydrofuran. This solution was maintained under stirring for one hour at −780° C., 12 g (44 mmol) of the methyl ketone obtained in Example 3, dissolved in 120 ml of tetrahydrofuran, were then added dropwise, and the mixture was maintained under stirring for one hour at −780° C. The reaction medium was then treated with 7.1 ml of diethyl chlorophosphate and was thereafter permitted to return to room temperature, at which it was stirred for 4 hours.

This reaction medium was then transferred to a solution of diisopropylamide (97.6 mmol) at −780° C. and was thereafter stirred for 15 hours at room temperature. The reaction medium was then poured into ice-cold water and thereafter acidified with 3N hydrochloric acid. After extraction with ethyl ether followed by conventional treatment of the organic phase, the residue was chromatographed on silica in a hexane/$CH_2Cl_2$ (95:15) mixture to yield 4.9 g (44w) of the expected compound, melting at 155° C.; $\alpha_D$=−4.2° (c=1, chloroform).

EXAMPLE 7:

Preparation of 1,2,3,4-tetrahydro-1,4a,9b-trimethyl-1,4methanodibenzofuran-8-yl bromomethyl ketone:

18 g (66 mmol) of the ketone obtained in Example 3 in 100 ml of dioxane and 100 ml of ether were treated by the dropwise addition of a solution of 3.4 ml of bromine in 35 ml of $CH_2Cl_2$. The reaction medium was maintained under stirring for 2 hours at room temperature, then poured into ice-cold water and extracted with 800 ml of ethyl ether. After drying and evaporation, the residue was chromatographed on silica in a hexane/$CH_2Cl_2$ (50:50) mixture. 19.75 g (80w) of the expected compound were obtained in the form of an orange-colored oil.

EXAMPLE 8:

Preparation of methyl 4-[(E)-3-(1,2,3,4-tetrahydro1, 4a,9b-trimethyl-1,4-methanodibenzofuran-8-yl)-3-oxo-1-propenyl]benzoate:

A solution containing 4 g (14.8 mmol) of (+)-THTMDBF-8-yl methyl ketone prepared as described in Example 3 and 2.42 g (14.7 mmol) of paramethoxycarbonylcarbaldehyde in 15 ml of methanol were treated with 500 mg of sodium hydroxide and 30 mg of crown ether (18-crown-6). The reaction medium was stirred at room temperature for 2 hours and was then poured into acidulated water. After extraction with 200 ml of ethyl ether followed by conventional treatment and chromatography on silica in a hexane/ether (80:20) mixture, 2.28 g (37w) of the expected compound, melting at 1240°–1260° C., were isolated; $\alpha_D$=+14.2° (c=0.54, ethanol).

EXAMPLE 9:

Preparation of 4-[(E)-3-(1,2,3,4-tetrahydro-1,4a,9b-trimethyl-1,4-methanodibenzofuran-8-yl)-3-oxo-1-propenyl]benzoic acid:

2.2 g (5.28 mmol) of the methyl ester obtained in Example 8 in 20 ml of methanol were treated with 1 g of sodium hydroxide. The reaction medium was maintained under stirring for 24 hours at room temperature.

The reaction medium was poured into ice-cold water, acidified to pH 1 with concentrated hydrochloric acid and extracted with ethyl acetate. The organic phase was washed with water, dried over magnesium sulfate and evaporated to yield, after chromatography on silica in the eluent $CH_2Cl_2$/methanol (95:5), 1.15 g (546) of the expected compound of melting point 225°–227° C.; $\alpha_D$=20.3° (c=1, ethanol).

EXAMPLE 10:

Preparation of methyl 4-[3-(1,2,3,4-tetrahydro-1,4a, 9b-trimethyl-1,4-methanodibenzofuran-8-yl)-3-oxopropynyl]benzoate:

1.48 g (4.85 mmol) of the chloride of 1,2,3,4-tetrahydro-1,4a,9b-trimethyl-1,4-methanodibenzofuran-8-carboxylic acid obtained in Example 5 in 20 ml of $CH_2Cl_2$ was treated dropwise at 0° C. with a solution containing 1.12 g (4.83 mmol) of methyl 4(trimethylsilylethynyl)benzoate and 2.26 g (17 mmol) of aluminum chloride. The reaction mixture was permitted to return to room temperature while stirring overnight. The reaction mixture was then poured into ice-cold acidulated water and thereafter extracted with 350 ml of ethyl ether.

After conventional treatment followed by chromatography on silica in the eluent $CH_2Cl_2$/hexane (80:20), 667 mg (33%) of the expected compound were isolated.

EXAMPLE 11:

Preparation of 4-[3-(1,2,3,4-tetrahydro-1,4a,9b-trimethyl-1,4-methanodibenzofuran-8-yl)-3-oxopropynyl]benzoic acid:

0.66 g of methyl ester obtained in Example 10 dissolved in 10 ml of tetrahydrofuran was treated with 200 mg of lithium hydroxide monohydrate.

The reaction mixture was heated to reflux for 6 h. After the same treatment as in Example 5, followed by recrystallization in cyclohexane, 200 mg of the expected compound of melting point 165°–170° C. were isolated.

EXAMPLE 12:

Preparation of 4-[2-(1,2,3,4-tetrahydro-1,4a,9b-trimethyl-1,4-methanodibenzofuran-8-yl)-2-oxoethoxy]benzoic acid:

Step (a): Preparation of benzyl 4-[2-(1,2,3,4-tetrahydro-1,4a,9b-trimethyl-1,4-methanodibenzofuran-8-yl)-2-oxoethoxy]benzoate:

4.57 g of benzyl para-hydroxybenzoate were added dropwise into a round-bottomed flask containing 605 mg of sodium hydride (80% in oil) suspended in 50 ml of dimethylformamide, and the mixture was maintained under stirring at room temperature for 2 hours. 7 g (20 ml) of the bromomethyl ketone obtained in Example 6 in 70 ml of dimethylformamide were then added dropwise to the reaction medium thus formed, and the mixture was maintained under stirring at room temperature for 4 hours. After the same treatment as in Example 2, and after chromatography on silica in an eluent gradient (hexane/$CH_2Cl_2$ from 30:70 to 20:80), 8.90 g (90%) of the expected compound were isolated.

Step (b):

Preparation of 4-[2-(1,2,3,4-tetrahydro-1,4a,9b-trimethyl-1,4-methanodibenzofuran-8-yl)-2-oxoethoxy]benzoic acid:

4.41 g (8.8 mmol) of the benzyl ester obtained in step (a) in 70 ml of dioxane were hydrogenated in the presence of 132 mg of palladium (10%) on charcoal at 60° C. at a hydrogen pressure of 7 bars for 8 hours. After filtration of the reaction medium through Celite and evaporation, the residue was chromatographed on silica in the eluent $CH_2Cl_2$/ethyl ether (95:5). After the product was converted into a paste in hexane, 2.63 g (73%) of the expected compound, melting at 187.5° C., were isolated.

EXAMPLE 13:

Preparation of 4-[2-(1,2,3,4-tetrahydro-1,4a,9b-trimethyl-1,4-methanodibenzofuran-8-yl)-2-hydroxyethoxy]benzoic acid:

4.41 g (8.9 mmol) of the benzyl ester obtained in Step (a) of Example 12 in 90 ml of dioxane were hydrogenated in the presence of 660 mg of palladium (10%) on charcoal at a hydrogen pressure of 7 bars at room temperature for 3 hours. After filtration of the reaction medium through Celite, evaporation and chromatography on silica in the eluent $CH_2Cl_2$/methanol (9:1), 1.60 g (63%) of the expected compound, melting at 123.20° C., was isolated.

EXAMPLE 14:

Preparation of benzyl 4-[2-(1,2,3,4-tetrahydro-1,4a,9b-trimethyl-1,4-methanodibenzofuran-8-yl)-2-hydroxybenzoate:

4.9 g (0.02 mmol) of benzyl 2,4-dihydroxybenzoate were introduced into a round-bottomed flask containing 0.6 g of sodium hydride at a concentration 80% in oil, suspended in 50 ml of dimethylformamide, and the mixture was maintained under stirring for 2 hours at room temperature. 7 g (0.02 mmol) of the bromomethyl ketone obtained in Example 7 were then added dropwise. The reaction medium was maintained under stirring for 3 hours at room temperature. After the same treatment as in Example 2, followed by chromatography on silica in the eluent hexane/$CH_2Cl_2$ (2:8) and recrystallization in hexane, 7.42 g (63o) of the expected compound, melting at 98.4° C., were isolated.

EXAMPLE 15:

Preparation of 4-[2-(1,2,3,4-tetrahydro-1,4a,9b-trimethyl-1,4-methanodibenzofuran-8-yl)-2-oxoethoxy]-2-hydroxybenzoic acid:

3.7 g (7.2 mmol) of the benzyl ester obtained in Example 14 dissolved in 50 ml of dioxane containing 0.1 ml of acetic acid were hydrogenated at a pressure of 7 bars in the presence of 110 mg of palladium (10 %) on charcoal for 3 hours at 600° C. After the same treatment as in Example 14, 2.19 g (72%) of the expected compound, melting at 186°–188° C., were isolated.

EXAMPLE 16:

Preparation of 4-[2-(1,2,3,4-tetrahydro-1,4a,9b-trimethyl-1,4-methanodibenzofuran-8-yl)-2-hydroxyethoxy-2-hydroxybenzoic acid:

3.67 g (7.16 mmol) of the benzyl ester obtained in Example 14 dissolved in 50 ml of dioxane were hydrogenated at a pressure of 7 bars of hydrogen in the presence of 550 mg of palladium (10%) on charcoal at room temperature for 4 hours.

After the same treatment as in Example 14, followed by recrystallization in a diisopropyl ether/hexane mixture, 1.81 g (60w) of the expected compound, melting at 168°–170° C., were isolated.

EXAMPLE 17:

Preparation of 4-[2-(1,2,3,4-tetrahydro-1,4a,9b-trimethyl-1,4-methanodibenzofuran-8-yl)ethoxy]-2-hydroxybenzoic acid:

2.05 g (4 mmol) of the benzyl ester obtained in Example 14 dissolved in 30 ml of dioxane were hydrogenated at a pressure of 7 bars at 70° C. for 6 hours. After the same treatment as in Example 14 followed by chromatography on silica in $CH_2Cl_2$, 0.83 g (51w) of the expected compound of melting point 212°–214° C. was isolated.

EXAMPLE 18:

Preparation of intermediates for ethyl 4-[(1,2,3,4-tetrahydro-1,4a,9b-trimethyl-1,4-methanodibenzofuran-8-yl)carbonyl]cinnamate:

EXAMPLE 18(a):

Preparation of methyl 4-[(1,2,3,4-tetrahydro-1,4a, 9b-trimethyl-1,4-methanodibenzofuran-8-yl) carbonyl]benzoate:

5.92 g (44 mmol) of aluminum chloride were added dropwise to a solution of 6.76 g (29.6 mmol) of (+)-THTMDBF and 5.72 g (28.8 mmol) of the acid chloride of methyl monoterephthalate in 130 ml of $CH_2Cl_2$, and the mixture was maintained under stirring at room temperature overnight.

After the same treatment as in Step (a) of Example 12, followed by chromatography on silica in the eluent mixture $CH_2Cl_2$/hexane (60:40), 4.47 g (40w) of the expected compound, melting at 150° C., were isolated.

EXAMPLE 18(b):

Preparation of 4-[(1,2,3,4-tetrahydro-1,4a,9b-trimethyl-1,4-methanodibenzofuran-8-yl)carbonyl] benzoic acid:

2.52 g (6.44 mmol) of the ester obtained in Example 18(a) dissolved in 30 ml of methanol were treated with 2.5 g of sodium hydroxide and heated to reflux for 3 hours. After the same treatment as in Example 5, followed by recrystallization in hexane, 2.35 g (97w) of the expected compound, melting at 262–264° C., were isolated; $\alpha_D = 22.1°$ (c=1, dimethylformamide).

EXAMPLE 18(c):

Preparation of 4-[(1,2,3,4-tetrahydro-1,4a,9b-trimethyl-1,4-methanodibenzofuran-8-yl) hydroxymethyl]phenylcarbinol:

A solution of 3.76 g (10 mmol) of the acid obtained in Example 18(b) was added dropwise to a suspension of 1.14 g of lithium aluminum hydride in 10 ml of tetrahydrofuran, and the mixture was maintained under stirring for 3 hours at room temperature. The reaction medium was neutralized at 0° C. by adding saturated ammonium chloride solution dropwise. The precipitate was filtered off, washed with hexane and dried to yield 3.13 g (86%) of the expected compound, melting at 113°–115° C.

EXAMPLE 18(d):

Preparation of 4-[(1,2,3,4-tetrahydro-1,4a,9b-trimethyl-1,4-methanodibenzofuran-8-yl) carbonyl] phenylcarbaldehyde:

3.1 g (8.5 mmol) of the diol obtained in Example 18(c) dissolved in 60 ml of $CH_2Cl_2$ were treated with 5.5 g of pyridinium chlorochromate. The reaction medium was maintained under stirring at room temperature for 3 hours. The reaction medium is then filtered through Celite. The organic phase was washed with saturated ammonium chloride solution, rinsed with water, dried and evaporated to yield, after chromatography on silica in the eluent mixture $CH_2Cl_2$/hexane (9:1), 2 g (66%) of the expected compound, melting at 138°–142° C.

EXAMPLE 19:

Preparation of ethyl 4-[(1,2,3,4-tetrahydro-1,4a,9b-trimethyl-1,4-methanodibenzofuran-8-yl)carbonyl] cinnamate:

1.65 ml (8.3 mmol) of ethyl diethylphosphonoacetate dissolved in 100 ml of tetrahydrofuran was treated with 500 mg of sodium hydride (80% in oil) and maintained under stirring for 2 hours at room temperature.

To this reaction medium, a solution containing 100 mg of crown ether (15-crown-S) and 2 g (5.5 mmol) of the aldehyde obtained in Example 18(d) dissolved in 30 ml of tetrahydrofuran was added. The reaction medium was maintained under stirring for 2 h, 30 min. at room temperature. The reaction medium was neutralized with 1N hydrochloric acid. The organic phase was washed, dried and evaporated. The residue was chromatographed on silica in $CH_2Cl_2$ and, after recrystallization in hexane, 2.18 g (75%) of the expected compound, melting at 115°–116° C., were isolated.

EXAMPLE 20:

Preparation of 4-[(1,2,3,4-tetrahydro-1,4a,9b-trimethyl-1,4-methanodibenzofuran-8-yl)carbonyl] cinnamic acid:

1.5 g (3.5 mmol) of the ethyl ester obtained in Example 19 was saponified under the conditions described in Example 9 to yield, after recrystallization in an ethanol/$H_2O$ (4:1) mixture, 1.2 g (85%) of the expected acid, melting at 242°–243° C.; $\alpha_D$=+11.2° (c=1, chloroform).

EXAMPLE 21:

Preparation of ethyl 2-[(E)-3-(1,2,3,4-tetrahydro-1,4a,9b-trimethyl-1,4-methanodibenzofuran-8-yl)-3-oxo-1-propenyl]-4-thiophenecarboxylate:

2.70 g (10 mmol) of the methyl ketone obtained in Example 3 were converted to chalcone in the presence of 1.7 g of 4-(ethoxycarbonyl)thiophenecarbaldehyde under the conditions described in Example 8 to yield, after recrystallization in ethyl acetate, 2.2 g (52%) of the expected compound, melting at 149°–151° C.

EXAMPLE 22:

Preparation of 2-[(E)-3-(1,2,3,4-tetrahydro-1,4a,9b-trimethyl-1,4-methanodibenzofuran-8-yl)-3-oxo-1-propenyl]-4-thiophenecarboxylic acid:

2.1 g (4.97 mmol) of the ethyl ester obtained in Example 21 were saponified under the conditions described in Example 8 to yield, after the same treatment and recrystallization in ethyl acetate, 1.5 g (75%) of the expected compound, melting at 226°–228° C.

EXAMPLE 23:

Preparation of 4-[(E)-3-(1,2,3,4-Tetrahydro-1,4a,9b-trimethyl-1,4-methanodibenzofuran-8-yl)-3-oxo-1-propenyl benzoic acid:

The same synthesis was carried out as in Example 9; starting from 2 g (4.8 mmol), 1 g (49w) of the expected levorotatory compound, melting at 227° C., are obtained; $\alpha_D$=–19.10 (c=1, ethanol).

EXAMPLE 24:

Biological activities of certain compounds described and exemplified above:

| COMPOUND OF EXAMPLE | Affinities for receptors Kd (nM)[a] | | | Antagonist activity with respect to the differentiation of F9 cells |
| --- | --- | --- | --- | --- |
| | RAR α | RAR β | RAR γ | ($IC_{50}$, nM)[b] |
| 12 | 3,200 | 745 | 481 | 40 |
| 13 | >3,200 | 230 | 40 | 36 |
| 15 | 2,500 | 114 | 150 | 55 |
| 17 | >10,000 | 315 | 2,250 | 270 |
| 23 | 220 | 53 | 27 | 19 |

[a]The affinites for the RARs were determined under the conditions described in B. Martin et al, "Selective Synthetic Ligands for Human Nuclear Retinoic Acid Receptors," Skin Pharmacol., 5, 57–65 (1992).
[b]The antagonist activity was determined by co-incubating a reference agonist [N-(4-carboxybenzyl)-5,6,7,8-tetrahydro-5,5,8,8-tetramethyl-2-naphthylamine (F9 $AC_{50}$ = 4nM)] and different concentrations of the test retinoid. These experiments were carried out under conditions for the determination of activity with respect to the differentiation of F9 cells according to the technique described in M. Darmon, M. Rocher, M. T. Cavey, B. Martin, T. Rabilloud, C. Delescluse and B. Shroot, "Biological activity of retinoids correlates with affinity for nuclear receptors, but not for cytosolic binding protein," Skin Pharmacol., 1, 161–175 (1988).

(B) EXAMPLES OF FORMULATIONS:
(1) ORAL ROUTE:

EXAMPLE 25:

The following composition was formulated in the form of a tablet weighing 0.8 g:

| | |
| --- | --- |
| Compound of Example 6 | 0.005 g |
| Pregelatinized satarch | 0.265 g |

-continued

| | |
|---|---|
| Microcrystalline cellulose | 0.300 g |
| Lactose | 0.200 g |
| Magnesium stearate | 0.030 g |

For the treatment of acne, 1 to 3 tablets daily were administered to an adult individual for 3 to 6 months, depending on the severity of the case under treatment.

EXAMPLE 26:

A suspension to be administered orally, to be packaged in 5 ml ampoules, was prepared:

| | |
|---|---|
| Compound of Example 15 | 0.050 g |
| Glycerol | 0.500 g |
| Sorbitol, 70% | 0.500 g |
| Saccharin sodium | 0.010 g |
| Methyl para-hydroxybenzoate | 0.040 g |
| Flavoring q.s. | |
| Purified water q.s. | 5 ml |

For the treatment of acne, 1 ampoule daily was administered to an adult individual for 3 months, depending on the severity of the case under treatment.

EXAMPLE 27:

The following formulation, to be packaged in hard gelatin capsules, was prepared:

| | |
|---|---|
| Compound of Example 16 | 0.025 g |
| Maize starch | 0.060 g |
| Lactose q.s. | 0.300 g |

The capsules were comprised of gelatin, titanium dioxide and a preservative.

For the treatment of psoriasis, 1 capsule daily was administered to an adult individual for 30 days.

(2) TOPICAL ROUTE:

EXAMPLE 28:

The following nonionic water-in-oil cream was prepared:

| | |
|---|---|
| Compound of Example 8 | 0.100 g |
| Mixture of refined oils, waxes and emulsive lanolin alcohols, marketed by BDF under the trademark "Anhydrous Eucerin" | 39.900 g |
| Methyl para-hydroxybenzoate | 0.075 g |
| Propyl para-hydroxybenzoate | 0.075 g |
| Sterile demineralized water q.s. | 100.000 g |

This cream was applied to psoriatic skin 1 to 2 times daily for 30 days.

EXAMPLE 29:

A gel was formulated from the following composition:

| | |
|---|---|
| Compound of Example 9 | 0.050 g |
| Erythromycin base | 4.000 g |
| Butylated hydroxytoluene | 0.050 g |
| Hydroxypropylcellulose marketed by Hercules under the trademark "KLUCEL HF" | 2.000 g |
| Ethanol (95° strength) q.s. | 100.000 g |

This gel was applied to a skin affected by dermatosis or a skin affected by acne 1 to 3 times daily for 6 to 12 weeks, depending on the severity of the case under treatment.

EXAMPLE 30:

An anti-seborrhoeic lotion was formulated by mixing the following ingredients:

| | |
|---|---|
| Compound of Example 10 | 0.030 g |
| Propylene glycol | 5.000 g |
| Butylated hydroxytoluene | 0.100 g |
| Ethanol (95° strength) q.s. | 100.000 g |

This lotion was applied twice daily to a seborrhoeic scalp, and a significant improvement was observed within a period of 2 to 6 weeks.

EXAMPLE 31:

A cosmetic composition for counteracting the adverse effects of sunlight was formulated by mixing the following ingredients:

| | |
|---|---|
| Compound of Example 12 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Perfume | 0.400 g |
| Demineralized water q.s. | 100.000 g |

This composition was applied daily; it was effective against photoinduced aging.

EXAMPLE 32:

The following nonionic oil-in-water cream was formulated:

| | |
|---|---|
| Compound of Example 13 | 0.500 g |
| Vitamin $D_3$ | 0.020 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. | 100.000 g |

This cream was applied to a psoriatic skin 1 to 2 times daily for 30 days.

EXAMPLE 33:

A topical gel was formulated by mixing the following ingredients:

| | |
|---|---|
| Compound of Example 15 | 0.050 g |
| Ethanol | 43.000 g |
| α-Tocopherol | 0.050 g |
| Carboxyvinyl polymer marketed under the trademark "Carbopol 941" by "Goodrich" | 0.500 g |
| Triethanolamine, as a 20% by weight aqueous solution | 3.800 g |
| Water | 9.300 g |
| Propylene glycol q.s. | 100.000 g |

This gel was applied in the treatment of acne 1 to 3 times daily for 6 to 12 weeks, depending on the severity of the case under treatment.

EXAMPLE 34:

A lotion for combating hair loss and for stimulating hair regrowth was formulated by mixing the following ingredients:

| | |
|---|---|
| Compound of Example 16 | 0.05 g |
| Compound marketed under the trademark "Minoxidil" | 1.00 g |
| Propylene glycol | 20.00 g |
| Ethanol | 34.92 g |
| Polyethylene glycol (molecular weight = 400) | 40.00 g |
| Butylated hydroxyanisole | 0.01 g |
| Butylated hydroxytoluene | 0.02 g |
| Water q.s. | 100.00 g |

This lotion was applied 2 times daily for 3 months to a scalp which had suffered considerable loss of hair.

EXAMPLE 35:

An anti-acne cream was formulated by mixing the following ingredients:

| | |
|---|---|
| Compound of Example 17 | 0.050 g |
| Retinoic acid | 0.010 g |
| Mixture of stearates of glycerol and polyethylene glycol (75 mol), marketed under the trademark "Gelot 64" by GATTEFOSSE | 15.000 g |
| Polyoxyethylenated kernel oil containing 6 mol of ethylene oxide, marketed under the trademark "Labrafil M2130 CS" by GATTEFOSSE | 8.000 g |
| Perhydrosqualene | 10.000 g |
| Preservatives | qs |
| Polyethylene glycol (molecular weight = 400) | 8.000 g |
| Ethylenediaminetetraacetic acid disodium salt | 0.050 g |
| Purified water q.s. | 100.000 g |

This cream was applied to a skin suffering from dermatosis or skin affected by acne 1 to 3 times daily for 6 to 12 weeks.

EXAMPLE 36:

An oil-in-water cream was formulated from the following composition:

| | |
|---|---|
| Compound of Example 19 | 0.020 g |
| Betamethasone 17-valerate | 0.050 g |
| S-Carboxymethylcysteine | 3.000 g |
| Polyoxyethylene stearate (40 mol of ethylene oxide) marketed under the trademark "Myrj 52" by ATLAS | 4.000 g |
| Polyoxyethylenesorbitan monolaurate containing 20 mol of ethylene oxide, marketed under the trademark "Tween 20" by ATLAS | 1.800 g |
| Mixture of glyceryl mono- and distearates, marketed under the trademark "Géléol" by GATTEFOSSE | 4.200 g |
| Propylene glycol | 10.000 g |
| Butylated hydroxyanisole | 0.010 g |
| Butylated hydroxytoluene | 0.020 g |
| Cetyl/stearyl alcohol | 6.200 g |
| Preservatives | q.s. |
| Perhydrosqualene | 18.000 g |
| Mixture of caprylic/capric triglycerides, marketed under the trademark "Miglyol 812" by DYNAMIT NOBEL | 4.000 g |
| Triethanolamine (99% by weight) | 2.500 g |
| Water q.s. | 100.000 g |

This cream was applied twice daily to a skin affected by dermatosis for 30 days.

EXAMPLE 37:

The following oil-in-water cream was formulated:

| | |
|---|---|
| Lactic acid | 5.000 g |
| Compound of Example 20 | 0.020 g |
| Polyoxyethylene stearate (40 mol of ethylene oxide) marketed under the trademark "Myrj 52" by ATLAS | 4.000 g |
| Polyoxyethylenesorbitan monolaurate containing 20 mol of ethylene oxide, marketed under the trademark "Tween 20" by ATLAS | 1.800 g |
| Mixture of glyceryl mono- and distearates, marketed under the trademark "Géléol" by GATTEFOSSE | 4.200 g |
| Propylene glycol | 10.000 g |
| Butylated hydroxyanisole | 0.010 g |
| Butylated hydroxytoluene | 0.020 g |
| Cetyl/stearyl alcohol | 6.200 g |
| Preservatives | q.s. |
| Perhydrosqualene | 18.000 g |
| Mixture of caprylic/capric triglycerides, marketed under the trademark "Miglyol 812" by DYNAMIT NOBEL | 4.000 g |
| Water q.s. | 100.000 g |

This cream was applied once daily; it assisted in combating aging, whether photoinduced or chronologic.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dibenzofuran compound having the structural formula (I):

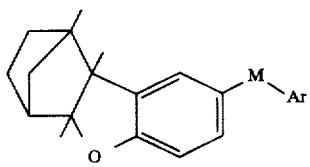
(I)

wherein Ar is a radical having one of the following formulae (II)–(VI):

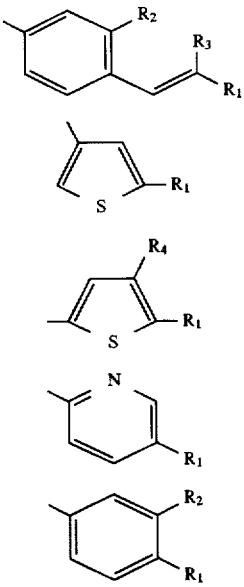

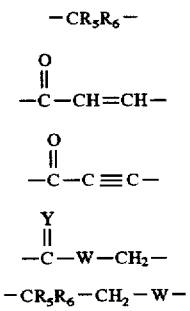

wherein M is a bivalent radical selected from among those of the following formulae, with the proviso that said formulae can be oriented from left to right or vice versa:

$$-CR_5R_6-\quad (a)$$

$$\underset{\|}{\overset{O}{\|}}\atop-C-CH=CH- \quad (b)$$

$$\underset{\|}{\overset{O}{\|}}\atop-C-C\equiv C- \quad (c)$$

$$\underset{\|}{\overset{Y}{\|}}\atop-C-W-CH_2- \quad (d)$$

$$-CR_5R_6-CH_2-W- \quad (e)$$

with the proviso that, when M is a radical of formula (a), Ar cannot be a radical of formula (VI); $R_1$ is:

(i) a hydrogen atom, (ii) a —$CH_3$ radical, (iii) a radical —$(CH_2)_m$—O—$R_8$, (iv) a radical —$OR_8$, (v) a radical

(vi) a radical —$S(O)_tR_9$, with m, t, $R_8$ and $R_9$ having the definitions given below; $R_2$ is a hydrogen atom or a radical —$OR_8$, with $R_8$ having the definition given below; $R_3$ is a hydrogen atom or a lower alkyl radical; $R_4$ has the same definition as $R_1$, with the proviso that at least one of the two radicals $R_1$ and $R_4$ is a hydrogen atom; $R_5$ and $R_6$ are independently a hydrogen atom, a lower alkyl radical or a radical —$(X)_n$—$(CH_2)_p$—$R_7$, with the proviso that $R_5$ and $R_6$ may together form an oxo (=O) group, a thioxo (=S) or oxime group, a group ($R_{11}$—O—N=), an epoxy or cyclopropyl group, a cycloalkyl group optionally substituted by a halogen atom or a lower alkyl radical, or a dioxolane (—O—$(CH_2)_qO$—) group wherein q is equal to 2 or 3, with X, n, p, $R_7$ and $R_{11}$ having the definitions given below; $R_7$ is a hydrogen atom or a radical —$(CO)_r$—$R_{10}$ with r and $R_{10}$ having the definitions given below; $R_8$ is a hydrogen atom, a lower alkyl radical or a lower acyl radical; $R_9$ is (i) a hydrogen atom, (ii) a radical —N(R'R"), or (iii) a radical —$OR_{11}$, with R', R" and $R_{11}$ having the definitions given below; $R_{10}$ is a hydrogen atom, an alkyl radical, an alkenyl radical, an alkynyl radical, an aryl radical, a radical —$OR_{11}$, or a radical —N(R'R"), with R', R" and $R_{11}$ having the definitions given below; $R_{11}$ is a hydrogen atom, an alkyl radical having from 1 to 20 carbon atoms, a mono- or polyhydroxyalkyl radical, an optionally substituted aryl or optionally substituted aralkyl radical, a sugar residue or an amino acid or peptide residue; R' and R", which may be identical or different, are each a hydrogen atom, a lower alkyl radical, a mono- or polyhydroxyalkyl radical, an optionally substituted aryl radical, an optionally substituted aralkyl radical or an amino acid or peptide or sugar residue, with the proviso that R' and R" may together form a heterocycle; W is an oxygen or sulfur atom or a group —$NR_{12}$, with $R_{12}$ having the definition given below; $R_{12}$ is a hydrogen atom or a —$CH_3$ radical; and X and Y are each independently an oxygen atom or a sulfur atom; m and p which are integers vary independently from 0 to 10, with the proviso that when $R_7$ is a radical (CO) (CO)$_r$—$R_{10}$ and $R_{10}$ is a radical —$OR_{11}$, p cannot be 0; n and r independently have the value 0 or 1; and t is equal to 0, 1 or 2.

2. A dibenzofuran compound as defined by claim 1, wherein formula (I), Ar has the structure (II).

3. A dibenzofuran compound as defined by claim 1, wherein formula (I), Ar has the structure (III).

4. A dibenzofuran compound as defined by claim 1, wherein formula (I), Ar has the structure (IV).

5. A dibenzofuran compound as defined by claim 1, wherein formula (I), Ar has the structure (V).

6. A dibenzofuran compoundd as defined by claim 1, wherein formula (I), Ar has the structure (VI).

7. A dibenzofuran compound as defined by claim 1, comprising a pharmaceutically acceptable salt thereof.

8. A dibenzofuran compound as defined by claim 1, wherein formula (I), the lower alkyl radical substituents are selected from among methyl, ethyl, isopropyl, butyl, tert-butyl and hexyl radicals.

9. A dibenzofuran compound as defined by claim 1, wherein formula (I), the lower acyl radical is selected from acetyl, propionyl and pivaloyl radicals.

10. A dibenzofuran compound as defined by claim 1, wherein formula (I), the monohydroxyalkyl radical substituents are selected from among 2-hydroxyethyl, 2-hydroxypropyl and 3-hydroxypropyl radicals.

11. A dibenzofuran compound as defined by claim 1, wherein formula (I), the polyhydroxyalkyl radical substituents are selected from among 2,3-dihydroxypropyl, 2,3,4-trihydroxybutyl, 2,3,4,5-tetrahydroxypentyl and pentaerythritol radicals.

12. A dibenzofuran compound as defined by claim 1, wherein formula (I), the aryl radical substituents are selected from among phenyl radicals optionally substituted by at least one halogen atom, or a hydroxyl or nitro functional group, or a methoxy group.

13. A dibenzofuran compound as defined by claim 1, wherein formula (I), the aralkyl radical substituents are selected from among benzyl and phenethyl radicals optionally substituted by at least one halogen atom, or a hydroxyl or nitro functional group, or a methoxy group.

14. A dibenzofuran compound as defined by claim 1, wherein formula (I), the sugar residue substituents are selected from among those of glucose, galactose, mannose and glucuronic acid.

15. A dibenzofuran compound as defined by claim 1, wherein formula (I), the heterocyclic radical substituents are selected from among piperidino, morpholino, pyrrolidino and piperazino radicals which are optionally substituted by a $C_1$-$C_6$ alkyl radical or a mono- or polyhydroxyalkyl radical.

16. A dibenzofuran compound as defined by claim 1, having the structural formula (Ia):

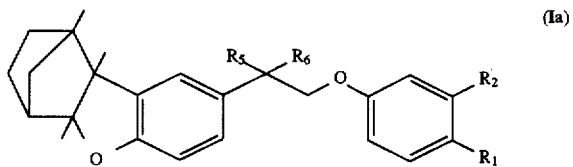

(Ia)

17. A dibenzofuran compound as defined by claim 1, selected from among methyl 4-[(E)-3-(1,2,3,4-tetrahydro-1,4a,9b-trimethyl-1,4-methanodibenzofuran-8-yl)-3-oxo-1-propenyl]benzoate; 4-[(E)-3-(1,2,3,4-tetrahydro-1,4a,9b-trimethyl-1,4-methanodibenzofuran-8-yl)-3-oxo-1-propenyl]benzoic acid; methyl 4-[(E)-3-(1,2,3,4-tetrahydro-1,4a,9b-trimethyl-1,4-methanodibenzofuran-8-yl)-3-oxo-1-propynyl]benzoate; 4-[(E)-3-(1,2,3,4-tetrahydro-1,4a,9b-trimethyl-1,4-methanodibenzofuran-8-yl)-3-oxo-1-propynyl]benzoic acid; benzyl 4-[2-(1,2,3,4-tetrahydro-1,4a,9b-trimethyl-1,4-methanodibenzofuran-8-yl)-2-oxoethoxy]benzoate; 4-[2-(1,2,3,4-tetrahydro-1,4a,9b-trimethyl-1,4-methanodibenzofuran-8-yl)-2-oxoethoxy]benzoic acid; 4-[2-(1,2,3,4-tetrahydro-1,4a,9b-trimethyl-1,4-methanodibenzofuran-8-yl)-2-hydroxyethoxy]benzoic acid; benzyl 4-[2-(1,2,3,4-tetrahydro-1,4a,9b-trimethyl-1,4-methanodibenzofuran-8-yl)-2-oxoethoxy]-2-hydroxybenzoate; 4-[2-(1,2,3,4-tetrahydro-1,4a,9b-trimethyl-1,4-methanodibenzofuran-8-yl)-2-oxoethoxy]-2-hydroxybenzoic acid; 4-[2-(1,2,3,4-tetrahydro-1,4a,9b-trimethyl-1,4-methanodibenzofuran-8-yl)-2-hydroxyethoxy]-2-hydroxybenzoic acid; 4-[2-(1,2,3,4-tetrahydro-1,4a,9b-trimethyl-1,4-methanodibenzofuran-8-yl)ethoxy]-2-hydroxybenzoic acid; ethyl 4-[(1,2,3,4tetrahydro-1,4a,9b-trimethyl-1,4-methanodibenzofuran-8-yl)carbonyl]cinnamate; 4-[(1,2,3,4-tetrahydro-1,4a,9b-trimethyl-1,4-methanodibenzofuran-8-yl)carbonyl]acid; ethyl 2-[(E)-3-(1,2,3,4-tetrahydro-1,4a,9b-trimethyl-1,4-methanodibenzofuran-8-yl)-3-oxo-1-propenyl]-4-thiophenecarboxylate; 2-[(E)-3-(1,2,3,4tetrahydro-1,4a,9b-trimethyl-1,4-methanodibenzofuran-8-yl)-3-oxo-1-propenyl]-4-thiophenecarboxylic acid; and 4[(E)-3-(1,2,3,4-tetrahydro-1,4a,9b-trimethyl-1,4-methanodibenzofuran-8-yl)-3-oxo-1-propenyl]benzoic acid.

18. A pharmaceutical composition of matter, comprising a therapeutically effective amount of a dibenzofuran compound as defined by claim 1, or pharmaceutically acceptable salt or isomer thereof, and a pharmaceutically acceptable carrier or diluent therefor.

19. The pharmaceutical composition as defined by claim 18, further comprising a retinoid compound, a D vitamin or derivative thereof, a corticosteroid, an anti-free radical agent, an α-hydroxy or α-keto acid or derivative thereof, an ion channel blocker, or combination thereof.

20. The pharmaceutical composition as defined by claim 18, comprising a tablet, a capsule, a syrup, a suspension, an elixir, a solution, a powder, granules, an emulsion, microspheres, nanospheres, lipid vesicles, polymeric vesicles, or an injectable.

21. The pharmaceutical composition as defined by claim 18, comprising an ointment, a cream, a milk, a pommade, an impregnated pad, a gel, a spray, or a lotion.

22. The pharmaceutical composition as defined by claim 18, adopted for topical administration.

23. The pharmaceutical composition as defined by claim 18, adopted for systemic administration.

24. The pharmaceutical composition as defined by claim 18, comprising from 0.001% to 5% by weight of said dibenzofuran compound, or salt or isomer thereof.

25. A method for treating a keratinization disorder in a mammalian organism in need of such treatment, comprising administering to such organism a therapeutically effective amount of the pharmaceutical composition as defined by claim 18.

26. A method for treating a dermalotogical disorder in a mammalian organism in need of such treatment, comprising administering to such organism a therapeutically effective amount of the pharmaceutical composition as defined by claim 18.

27. A method for treating an ophthalmological disorder in a mammalian organism in need of such treatment, comprising administering to such organism a therapeutically effective amount of the pharmaceutical composition as defined by claim 18.

28. A method for treating skin aging in a mammalian organism in need of such treatment, comprising administering to such organism a therapeutically effective amount of the pharmaceutical composition as defined by claim 18.

29. A method for treating epidermal and/or dermal atrophy in a mammalian organism in need of such treatment, comprising administering to such organism a therapeutically effective amount of the pharmaceutical composition as defined by claim 18.

30. A method for treating a cicatrization disorder in a mammalian organism in need of such treatment, comprising administering to such organism a therapeutically effective amount of the pharmaceutical composition as defined by claim 18.

31. A method for treating a sebaceous function disorder in a mammalian organism in need of such treatment, comprising administering to such organism a therapeutically effective amount of the pharmaceutical composition as defined by claim 18.

32. A method for treating a cancerous or precancerous disease state in a mammalian organism in need of such treatment, comprising administering to such organism a therapeutically effective amount of the pharmaceutical composition as defined by claim 18.

33. A method for treating inflammation in a mammalian organism in need of such treatment, comprising administering to such organism a therapeutically effective amount of the pharmaceutical composition as defined by claim 18.

34. A method for treating a dermatological, rheumatic, respiratory, or ophthalmologic disorder in a mammalian organism in need of such treatment, comprising administering to such organism a therapeutically effective amount of the pharmaceutical composition as defined by claim 18.

35. The method as defined by claim 34, comprising administering to such organism a daily dose of said dibenzofuran compound of about 0.01 mg/kg to 100 mg/kg of body weight thereof.

36. A cosmetic composition of matter, comprising a cosmetically effective amount of a dibenzofuran compound as defined by claim 1, or cosmetically acceptable salt or isomer thereof, and a cosmetically acceptable carrier or diluent therefor.

37. The cosmetic composition as defined by claim 36, comprising a cream, a milk, a lotion, a gel, microspheres, nanospheres, lipid vesicles, polymeric vesicles, a soap, or a shampoo.

38. The cosmetic composition as defined by claim 36, comprising from 0.00.1% to 3% by weight of said dibenzofuran compound, or salt or isomer thereof.

39. The cosmetic composition as defined by claim 36, further comprising a retinoid compound, a D vitamin or derivative thereof, a corticosteroid, an anti-free radical agent, an α-hydroxy or α-keto acid or derivative thereof, an ion channel blocker, or combination thereof.

40. A method for treating a skin or hair disorder on a mammalian organism in need of such treatment, comprising administering to such organism a cosmetically/therapeutically effective amount of the cosmetic composition as defined by claim 35.

41. The pharmaceutical composition as defined by claim 18, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraytnoic or 5,8,11-eicosatrynoic acid or ester or amide thereof, or combination thereof.

42. The pharmaceutical composition as defined by claim 18, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

43. The cosmetic composition as defined by claim 36, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11-14-eicosatetraynoic or 5,8,11-eicosatrynoic acid or ester or amide thereof, or combination thereof.

44. The cosmetic composition as defined by claim 36, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *

UNITED STATES PATENT AND TRADEMARK OFFICE
CERTIFICATE OF CORRECTION

PATENT NO. : 5,747,530  Page 1 of 8
DATED : May 5, 1998
INVENTOR(S) : Bruno Charpentier et al.

It is certified that error appears in the above-identified patent and that said Letters Patent is hereby corrected as shown below:

At column 4, line 20, please change "(1, 2, 3, 4-tetrahydro-1, 4a, 9b-" to --(1, 2, 3, 4, 4a, 9b-hexahydro-1, 4a, 9b- --.

At column 4, line 22 please change "(1, 2, 3, 4-Tetrahydro-1, 4a, 9b-" to --(1, 2, 3, 4, 4a, 9b-hexahydro-1, 4a, 9b- --.

At column 4, line 24, please change "(1, 2, 3, 4-tetrahydro-1, 4a, 9b-" to --(1, 2, 3, 4, 4a, 9b-hexahydro-1, 4a, 9b- --.

At column 4, line 26, please change "(1, 2, 3, 4-Tetrahydro-1, 4a, 9b-" to --(1, 2, 3, 4, 4a, 9b-hexahydro-1, 4a, 9b- --.

At column 4, line 29, please change "(1, 2, 3, 4-tetrahydro-1, 4a, 9b-" to --(1, 2, 3, 4, 4a, 9b-hexahydro-1, 4a, 9b- --.

At column 4, line 31, please change "(1, 2, 3, 4-Tetrahydro-1, 4a, 9b-" to --(1, 2, 3, 4, 4a, 9b-hexahydro-1, 4a, 9b- --.

At column 4, line 33, please change "(1, 2, 3, 4-Tetrahydro-1, 4a, 9b-" to --(1, 2, 3, 4, 4a, 9b-hexahydro-1, 4a, 9b- --.

At column 4, line 35, please change "(1, 2, 3, 4-tetrahydro-1, 4a, 9b-" to --(1, 2, 3, 4, 4a, 9b-hexahydro-1, 4a, 9b- --.

At column 4, line 38, please change "(1, 2, 3, 4-Tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530

DATED : May 5, 1998

INVENTOR(S) : Bruno Charpentier et al.

It is certified that error appears in the above-identified patent and that said Letters Patent is hereby corrected as shown below:

At column 4, line 41, please change "(1, 2, 3, 4-Tetrahydro-1, 4a, 9b-" to --(1, 2, 3, 4, 4a, 9b-hexahydro-1, 4a, 9b- --.

At column 4, line 44, please change "(1, 2, 3, 4-Tetrahydro-1, 4a, 9b-" to --(1, 2, 3, 4, 4a, 9b-hexahydro-1, 4a, 9b- --.

At column 4, line 46, please change "(1, 2, 3, 4-tetrahydro-1, 4a, 9b-" to --(1, 2, 3, 4, 4a, 9b-hexahydro-1, 4a, 9b- --.

At column 4, line 48, please change "(1, 2, 3, 4-Tetrahydro-1, 4a, 9b-" to --(1, 2, 3, 4, 4a, 9b-hexahydro-1, 4a, 9b- --.

At column 4, line 50, please change "(1, 2, 3, 4-tetrahydro-1, 4a, 9b-" to --(1, 2, 3, 4, 4a, 9b-hexahydro-1, 4a, 9b- --.

At column 4, line 53, please change "(1, 2, 3, 4-Tetrahydro-1, 4a, 9b-" to --(1, 2, 3, 4, 4a, 9b-hexahydro-1, 4a, 9b- --.

At column 4, line 56, please change "(1, 2, 3, 4-Tetrahydro-1, 4a, 9b-" to --(1, 2, 3, 4, 4a, 9b-hexahydro-1, 4a, 9b- --.

At column 4, line 60, please change "(1, 2, 3, 4-tetrahydro-1, 4a, 9b-" to --(1, 2, 3, 4, 4a, 9b-hexahydro-1, 4a, 9b- --.

At column 5, line 14, please change "1, 2, 3, 4-tetrahydro-1, 4a, 9b-" to --1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530
DATED : May 5, 1998
INVENTOR(S) : Bruno Charpentier et al.

Page 3 of 8 is certified that error appears in the above-identified patent and that said Letters Patent is hereby orrected as shown below:

At column 15, line 47, please change "1, 2, 3, 4-tetrahydro-1, 4a, 9b-" to --1, 2, 3, 4, 4a, 9b-hexahydro-1, 4a, 9b- --.

At column 16, line 12, please change "1, 2, 3, 4-tetrahydro-1, 4a, 9b-" to --1, 2, 3, 4, 4a, 9b-hexahydro-1, 4a, 9b- --.

At column 16, line 15, please change "1, 2, 3, 4-tetrahydro-1, 4a, 9b-" to --1, 2, 3, 4, 4a, 9b-hexahydro-1, 4a, 9b- --.

At column 16, line 30, please change "1, 2, 3, 4-tetrahydro-1, 4a, 9b-" to --1, 2, 3, 4, 4a, 9b-hexahydro-1, 4a, 9b- --.

At column 16, line 47, please change "1, 2, 3, 4-Tetrahydro-1, 4a, 9b-" to --1, 2, 3, 4, 4a, 9b-hexahydro-1, 4a, 9b- --.

At column 16, line 63, please change "1, 2, 3, 4-tetrahydro-1, 4a, 9b-" to --1, 2, 3, 4, 4a, 9b-hexahydro-1, 4a, 9b- --.

At column 17, line 16, please change "1, 2, 3, 4-tetrahydro-1, 4a, 9b-" to --1, 2, 3, 4, 4a, 9b-hexahydro-1, 4a, 9b- --.

At column 17, line 43, please change "1, 2, 3, 4-tetrahydro-1, 4a, 9b-" to --1, 2, 3, 4, 4a, 9b-hexahydro-1, 4a, 9b- --.

At column 17, lines 58-59, please change "(1, 2, 3, 4-tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530

DATED : May 5, 1998

INVENTOR(S) : Bruno Charpentier et al.

It is certified that error appears in the above-identified patent and that said Letters Patent is hereby corrected as shown below:

At column 18, line 8, please change "(1, 2, 3, 4-tetrahydro-1, 4a, 9b-" to --(1, 2, 3, 4, 4a, 9b-hexahydro-1, 4a, 9b- --.

At column 18, lines 27-28, please change "(1, 2, 3, 4-tetrahydro-1, 4a, 9b-" to --(1, 2, 3, 4, 4a, 9b-hexahydro-1, 4a, 9b- --.

At column 18, line 46, please change "(1, 2, 3, 4-tetrahydro-1, 4a, 9b-" to --(1, 2, 3, 4, 4a, 9b-hexahydro-1, 4a, 9b- --.

At column 18, line 59, please change "(1, 2, 3, 4-tetrahydro-1, 4a, 9b-" to --(1, 2, 3, 4, 4a, 9b-hexahydro-1, 4a, 9b- --.

At column 18, lines 63-64, please change "(1, 2, 3, 4-tetrahydro-1, 4a, 9b-" to --(1, 2, 3, 4, 4a, 9b-hexahydro-1, 4a, 9b- --.

At column 19, line 14, please change "(1, 2, 3, 4-tetrahydro-1, 4a, 9b-" to --(1, 2, 3, 4, 4a, 9b-hexahydro-1, 4a, 9b- --.

At column 19, line 29, please change "(1, 2, 3, 4-tetrahydro-1, 4a, 9b-" to --(1, 2, 3, 4, 4a, 9b-hexahydro-1, 4a, 9b- --.

At column 19, lines 43-44, please change "(1, 2, 3, 4-tetrahydro-1, 4a, 9b-" to --(1, 2, 3, 4, 4a, 9b-hexahydro-1, 4a, 9b- --.

At column 19, line 61, please change "(1, 2, 3, 4-tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530
DATED : May 5, 1998
INVENTOR(S) : Bruno Charpentier et al.

It is certified that error appears in the above-identified patent and that said Letters Patent is hereby corrected as shown below:

At column 20, line 7, please change "(1, 2, 3, 4-tetrahydro-1, 4a, 9b-" to --(1, 2, 3, 4, 4a, 9b-hexahydro-1, 4a, 9b- --.

At column 20, line 23, please change "(1, 2, 3, 4-tetrahydro-1, 4a, 9b-" to --(1, 2, 3, 4, 4a, 9b-hexahydro-1, 4a, 9b- --.

At column 20, lines 36-37, please change "(1, 2, 3, 4-tetrahydro-1, 4a, 9b-" to --(1, 2, 3, 4, 4a, 9b-hexahydro-1, 4a, 9b- --.

At column 20, lines 42-43, please change "(1, 2, 3, 4-tetrahydro-1, 4a, 9b-" to --(1, 2, 3, 4, 4a, 9b-hexahydro-1, 4a, 9b- --.

At column 20, line 57, please change "(1, 2, 3, 4-tetrahydro-1, 4a, 9b-" to --(1, 2, 3, 4, 4a, 9b-hexahydro-1, 4a, 9b- --.

At column 21, line 2, please change "(1, 2, 3, 4-tetrahydro-1, 4a, 9b-" to --(1, 2, 3, 4, 4a, 9b-hexahydro-1, 4a, 9b- --.

At column 21, line 16, please change "(1, 2, 3, 4-tetrahydro-1, 4a, 9b-" to --(1, 2, 3, 4, 4a, 9b-hexahydro-1, 4a, 9b- --.

At column 21, line 32, please change "(1, 2, 3, 4-tetrahydro-1, 4a, 9b-" to --(1, 2, 3, 4, 4a, 9b-hexahydro-1, 4a, 9b- --.

At column 21, line 53, please change "(1, 2, 3, 4-tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530

DATED : May 5, 1998

INVENTOR(S) : Bruno Charpentier et al.

It is certified that error appears in the above-identified patent and that said Letters Patent is hereby corrected as shown below:

At column 21, line 62, please change "(1, 2, 3, 4-tetrahydro-1, 4a, 9b-" to --(1, 2, 3, 4, 4a, 9b-hexahydro-1, 4a, 9b- --.

At column 22, line 8, please change "(1, 2, 3, 4-tetrahydro-1, 4a, 9b-" to --(1, 2, 3, 4, 4a, 9b-hexahydro-1, 4a, 9b- --.

At column 22, line 20, please change "(1, 2, 3, 4-Tetrahydro-1, 4a, 9b-" to --(1, 2, 3, 4, 4a, 9b-hexahydro-1, 4a, 9b- --.

At column 29, lines 28-29, please change "(1, 2, 3, 4-tetrahydro-1, 4a, 9b-" to --(1, 2, 3, 4, 4a, 9b-hexahydro-1, 4a, 9b- --.

At column 29, line 30, please change "(1, 2, 3, 4-tetrahydro-1, 4a, 9b-" to --(1, 2, 3, 4, 4a, 9b-hexahydro-1, 4a, 9b- --.

At column 29, lines 32-33, please change "(1, 2, 3, 4-tetrahydro-1, 4a, 9b-" to --(1, 2, 3, 4, 4a, 9b-hexahydro-1, 4a, 9b- --.

At column 29, line 34, please change "(1, 2, 3, 4-tetrahydro-1, 4a, 9b-" to --(1, 2, 3, 4, 4a, 9b-hexahydro-1, 4a, 9b- --.

At column 29, lines 36-37, please change "(1, 2, 3, 4-tetrahydro-1, 4a, 9b-" to --(1, 2, 3, 4, 4a, 9b-hexahydro-1, 4a, 9b- --.

At column 29, line 38, please change "(1, 2, 3, 4-tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530
DATED : May 5, 1998
INVENTOR(S) : Bruno Charpentier et al.

It is certified that error appears in the above-identified patent and that said Letters Patent is hereby corrected as shown below:

At column 29, line 40, please change "(1, 2, 3, 4-tetrahydro-1, 4a, 9b-" to --(1, 2, 3, 4, 4a, 9b-hexahydro-1, 4a, 9b- --.

At column 29, line 42, please change "(1, 2, 3, 4-tetrahydro-1, 4a, 9b-" to --(1, 2, 3, 4, 4a, 9b-hexahydro-1, 4a, 9b- --.

At column 29, line 44, please change "(1, 2, 3, 4-tetrahydro-1, 4a, 9b-" to --(1, 2, 3, 4, 4a, 9b-hexahydro-1, 4a, 9b- --.

At column 29, line 46, please change "(1, 2, 3, 4-tetrahydro-1, 4a, 9b-" to --(1, 2, 3, 4, 4a, 9b-hexahydro-1, 4a, 9b- --.

At column 29, lines 48-49, please change "(1, 2, 3, 4-tetrahydro-1, 4a, 9b-" to --(1, 2, 3, 4, 4a, 9b-hexahydro-1, 4a, 9b- --.

At column 29, lines 50-51, please change "(1, 2, 3, 4-tetrahydro-1, 4a, 9b-" to --(1, 2, 3, 4, 4a, 9b-hexahydro-1, 4a, 9b- --.

At column 29, line 52, please change "(1, 2, 3, 4-tetrahydro-1, 4a, 9b-" to --(1, 2, 3, 4, 4a, 9b-hexahydro-1, 4a, 9b- --.

At column 29, line 54, please change "(1, 2, 3, 4-tetrahydro-1, 4a, 9b-" to --(1, 2, 3, 4, 4a, 9b-hexahydro-1, 4a, 9b- --.

At column 29, line 56, please change "(1, 2, 3, 4-tetrahydro-1, 4a, 9b-" to --(1, 2, 3, 4, 4a, 9b-hexahydro-1, 4a, 9b- --.

UNITED STATES PATENT AND TRADEMARK OFFICE
CERTIFICATE OF CORRECTION

PATENT NO. : 5,747,530

DATED : May 5, 1998

INVENTOR(S) : Bruno Charpentier et al.

It is certified that error appears in the above-identified patent and that said Letters Patent is hereby corrected as shown below:

At column 29, lines 58-59, please change "(1, 2, 3, 4-tetrahydro-1, 4a, 9b-" to --(1, 2, 3, 4, 4a, 9b-hexahydro-1, 4a, 9b- --.

At column 19, line 4, please delete "Example 6" and insert --Example 7--.

At column 21, line 41, please delete "(15-crown-S)" and insert --(15-crown-5).

At column 4, line 32, please delete "b acid" and insert --benzoic acid--.

Signed and Sealed this

Twenty-eighth Day of September, 1999

Attest:

Q. TODD DICKINSON

*Attesting Officer*  *Acting Commissioner of Patents and Trademarks*